United States Patent [19]

Ax

[11] Patent Number: 4,683,213

[45] Date of Patent: Jul. 28, 1987

[54] METHOD FOR PREDICTING THE FERTILITY OF MALE MAMMALS

[75] Inventor: Roy L. Ax, Mazomanie, Wis.

[73] Assignee: Wisconsin Alumni Research Foundation, Madison, Wis.

[21] Appl. No.: 725,569

[22] Filed: Apr. 22, 1985

[51] Int. Cl.$^4$ ............................................ G01N 33/53
[52] U.S. Cl. .................................... 436/501; 435/806; 436/63; 436/503; 436/504; 436/906
[58] Field of Search ............... 436/501, 503, 504, 906, 436/63; 435/29, 806

[56] References Cited

PUBLICATIONS

N. A. C. Cressie and D. D. Keightley, (1979), "The Underlying Structure of the Direct Linear Plot With Application to the Analysis of Hormone–Receptor Interactions", *J. Steroid Biochem.*, 11, 1173.

D. Rodbard, (1976), "Estimation of Molecular Weight by Gel Filtration and Gel Electrophoresis, II. Statistical and Computational Considerations", *Methods of Protein Separation*, vol. 2, N. Catsimpoolas, ed. (Plenum Press, NY), Ch. 4.

J. M. Bedford (1970), "Sperm Capacitation and Fertilization in Mammals", *Biol. Reprod.*, Supp. 2, 128–158.

S. Aonuma, et al., (1973), "Studies on Sperm Capacitation: I. The Relationship Between a Guinea Pig Sperm Coating Antigen and a Sperm Capacitation Phenomenon", *Reprod. Fertil.*, 35 425–432.

D. W. Fawcett, (1975), "The Mammalian Spermatozoon", *Dev., Bio.*, 44, 394–436.

R. Yanagimachi, (1978), "Sperm—Egg Association in Mammals", *Curr. Top. Dev. Biol.*, 12, 83–105.

C. N. Lee, R. W. Lenz, and R. L. Ax (1983), "Bovine Sperm Undergo Capacitation when Exposed to Glycosaminoglycans In Vitro", *75th Ann. Mtng. Soc. Anim. Sci.*, Abstract 530.

R. W. Lenz, M. E. Bellin, and R. L. Ax, (1983), "Rabbit Spermatozoa Undergo an Acrosome Reaction in the Presence of Glycosaminoglycans", *Gamete Res.*, 8, 11.

H. G. Grimek and R. L. Ax, (1982), "Chromatographic Comparison of Chondroitin-Containing Proteoglycan from Small and Large Bovine Ovarian Follicles", *Biochem. Biophys. Res. and Comm.*, 104, 1401.

C. N. Lee and R. L. Ax (1984), "Concentrations and Composition of Glycosaminoglycans in the Female Bovine Reproductive Tract", *J. Dairy Sci.*, G7, 2006–2009.

R. L. Ax, K. Dickson, and R. W. Lenz, (1985), "Induction of the Acrosome Reaction in Response to Chondroitin Sulfates In Vitro is Related to Non-Return Rates of Dairy Bulls", *J. Dairy Sci.*, 68, 387–390.

N. N. Delgado, et al. (1982), "Heparin Binding Sites in the Human Spermatozoa Membrane", *Arch. Androl.*, 8, 87.

R. R. Handrow, et al. (1984), "Specific Binding of the Glycosaminoglycan $^3$H–Heparin to Bull, Monkey, and Rabbit Spermatozoa In Vitro", *J. Androl.*, 5, 51.

G. H. Barlow (1983), "Molecular Weight Distribution Determination on Heparin Samples", *Thromb. Res.*, 31, 513.

L. Kjellen, et al., (1977), "Binding of Heparin and Heparan Sulfate to Rat Liver Cells", *Biochem. Biophys. Res. Comm.*, 74, 126.

C. Labarca and K. Paigen, (1980), "A Simple, Rapid, and Sensitive DNA Assay Procedure", *Anal. Biochem.*, 102, 344.

*Primary Examiner*—Sidney Marantz
*Assistant Examiner*—David A. Saunders
*Attorney, Agent, or Firm*—David J. Houser

[57] ABSTRACT

A method for evaluating the fertility of a test male mammal relative to the fertility of a control male mammal. The method includes the steps of collecting samples of semen from the test male and the control male. The binding affinity of a selected glycosaminoglycan to the sperm of the semen samples is measured by a selected means for measuring binding affinities. The fertility of the test male may be evaluated as higher or lower than that of the control male by the degree to which the binding affinity of the glycosaminoglycan to its sperm is higher or lower than the binding affinity of the glycosaminoglycan to the sperm of the control male.

14 Claims, 3 Drawing Figures

4,683,213

METHOD FOR PREDICTING THE FERTILITY OF MALE MAMMALS

TECHNICAL FIELD

The present invention relates to methods for predicting fertility of male mammals in general and, in particular, to such methods that utilize an examination of physical traits of sperm taken from the animal to be evaluated.

BACKGROUND OF ART

In various contexts, it is useful to be able to predict the fertility of a male mammal. Thus, animal breeders are concerned to use males likely produce offspring of desirable genetic traits. However, it is also important to such animal breeders that fertilization actually take place as a consequence of any given attempt to artificially inseminate a female. For example, in the bovine artificial insemination industry, bulls are evaluated on the basis of the milk production and other characteristics of their daughters. However, a bull of low fertility, as measured by the number of times a cow must be artificially inseminated before pregnancy occurs, is of reduced value. In extreme cases, such bulls are disposed of.

Currently, in the bovine artificial insemination industry, bulls are evaluated for fertility by a process that takes from five to six years to complete. When a breeder examines a one-year-old, sexually mature bull, the breeder's only source of information about the bull's fertility is the pedigree information available on the animal. Testicular size and other gross physical characteristics of the animal provide little or no useful information relating to fertility. Typically such a bull first is bred to cows until as many as 200 daughters are produced and monitored for milk production. It takes as much as four years to do this, because the daughters themselves must become sexually mature so that they can be impregnated, calve, and begin to produce milk. If daughter milk production is good, the bull is kept and included in the breeder's general breeding program. Only at that time is the bull bred to a population of cows sufficiently large for the breeder to judge its fertility.

If a bull's fertility is found to be unacceptably low, the bull is disposed of. Typically, only one out of seven bulls are kept after evaluation of the bull's progeny and fertility has been completed. In the meantime, the breeder has spent a large amount of money and time to maintain and breed the bulls that have been eliminated. If at least some of the bulls destined to be eliminated could be detected as being of low fertility early in the evaluation process, considerable money could be saved.

In other contexts, it is also useful to evaluate quickly the fertility of a breeding male. Breeding males for various types of animals are sold for use in a farmer's herd or for addition to the stud string of an artificial inseminator. Presently there is no widely used method of evaluating fertility of an animal so sold unless statistical data has been amassed on the animal's past production. The purchase of such animals tends to be blind speculation, at least with regard to fertility. The availability of a method for evaluating fertility in a short period of time could thus be of value both to the seller who desires to substantiate the reasonableness of a high price for his animal and to the buyer who wants to know in advance what he is getting.

It would be advantageous in other contexts to be able to test male fertility without having to monitor actual impregnations. Thus, medical personnel concerned with human fertility can evaluate the sperm count of a male but have no generally used, effective conventional means of evaluating the capability of that sperm to fertilize an ovum in vivo. Similarly, it would be desirable to be able to evaluate the fertility of male zoo animals and other animals in which fertility cannot be determined conveniently, economically, or in a socially practical way by attempted fertilization of large numbers of females.

Before mammalian spermatozoa are capable of fertilizing ova, they must undergo capacitation and the acrosome reaction. In vivo, capacitation occurs when mammalian spermatozoa reside for a time in the female reproductive tract. See J. M. Bedford (1970), "Sperm Capacitation and Fertilization in Mammals." *Biol. Reprod.*, Supp. 2, 128–158. Capacitation seems to require the removal of components from the spermatozoa that are epididymal or seminal plasmatic in origin. See S. Aonuma, et al. (1973), "Studies on Sperm Capacitation: I. The Relationship Between a Guinea Pig Sperm Coating Antigen and a Sperm Capacitation Phenomenon." *Reprod. Fertil.*, 35 425–432. After capacitation has occurred, the sperm are able to undergo the acrosome reaction. The acrosome reaction releases enzymes that digest the matrix of the cumulus cells surrounding the ovum. This digestion of the matrix permits the zona pellucida to be penetrated by spermatozoa, so that the sperm may make their way toward the ovum. See D. W. Fawcett (1975), "The Mammalian Spermatozoon." *Dev. Bio.*, 44, 394–436; and R. Yanagimachi (1978), "Sperm-Egg Association in Mammals." *Curr. Top. Dev. Biol.*, 12, 83–105.

It is believed that gycosaminoglycans (hereinafter GAGs) enhance capacitation or at least enhance the incidence of acrosome reactions in mammals. See C. N. Lee, R. W. Lenz, and R. L. Ax (1983), "Bovine Sperm Undergo Capacitation When Exposed to Glycosaminoglycans In Vitro." 75*th Ann. Mtng. Soc. Anim. Sci.* Abstract 530; and R. W. Lenz, M. E. Bellin, and R. L. Ax (1983), "Rabbit Spermatozoa Undergo and Acrosome Reaction in the Presence of Glycosaminoglycans." *Gamete Res.*, 8, 11. GAGs are found in follicular fluid (H. G. Grimek and R. L. Ax [1982], "Chromatographic Comparison of Chondroitin-Containing Proteoglycan from Small and Large Bovine Ovarian Follicles." *Biochem. Biophys. Res. and Comm.*, 104, 1401.), and in all regions of the bovine female reproductive tract (C. N. Lee and R. L. Ax [1984], "Concentrations of Glycosaminoglycans in the Female Bovine Reproductive Tract." *J. Dairy Sci.*, G7, 2006–2009. Consequently, it is likely that they play an important role in vivo to capacitate sperm. Nevertheless, it is not known precisely what components of the female reproductive tract enhance the ability of sperm to undergo capacitation and the acrosome reaction. R. L. Ax, K. Dickson, and R. W. Lenz (1985), "Induction of the Acrosome Reaction in Response to Chondroitin Sulfates In Vitro Is Related to Non-return Rates of Dary Bulls." *J. Dairy Sci.*, 68, 387–390, have reported that nonreturn rates for bulls used in the artificial insemination industry corresponded to the effectiveness with which acrosome reactions could be induced in vitro by a GAG.

It is knwon that certain GAGs specifically bind to mammalian sperm. Thus, specific binding of the radioactively tagged GAG $^3$H-heparin has been reported for human, bovine, rabbit, and monkey sperm. See N. N. Delgado, et al. (1982), "Heparin Binding Sites in the Human Spermatozoa Membrane." *Arch. Androl.*, 8, 87; and R. R. Handrow, et. al. (1984), "Specific Binding of the Glycosaminoglycan $^3$H-Heparin to Bull, Monkey, and Rabbit Spermatozoa In Vitro." *J. Androl*, 5, 51. The binding interaction observed was typical of a receptor-ligand interaction such that dissociation constants could be determined, together with a determination of the number of heparin binding sites on the sperm.

BRIEF SUMMARY OF THE INVENTION

The method of the invention is summarized in that a method for evaluating the fertility of a test male mammal relative to the fertility of a control male mammal includes the following steps. First, samples of semen are collected from the test male and the control male. Then, the binding affinity of a selected glycosaminoglycan to the sperm of the semen samples is measured by a selected means for measuring binding affinities. By this method, the fertility of the test male may be evaluated as higher or lower than that of the control male by the degree to which the binding affinity of the glycosaminoglycan to its sperm is higher or lower than the binding affinity of the glycosaminoglycan to the sperm of the control male.

A primary object of the invention is to provide a method for evaluating the fertility of a male mammal by direct examination of the sperm thereof.

A second object of the invention is to provide for such a method that utilizes objective measurement of physical characteristics of the sperm.

An additional object of the invention is to provide such a method adapted to evaluate the fertility of a male mammal within a conveniently short period of time.

Other objects, features, and advantages of the invention will be apparent from the following detailed description of a preferred embodiment of a method exemplifying the principles of the invention.

BRIEF DESCRIPTION OF THE DRAWINGS

The figures are graphical presentations of data discussed in the Detailed Description of the Preferred Embodiment.

DETAILED DESCRIPTION OF THE PRFERRED EMBODIMENT

Figure 1:
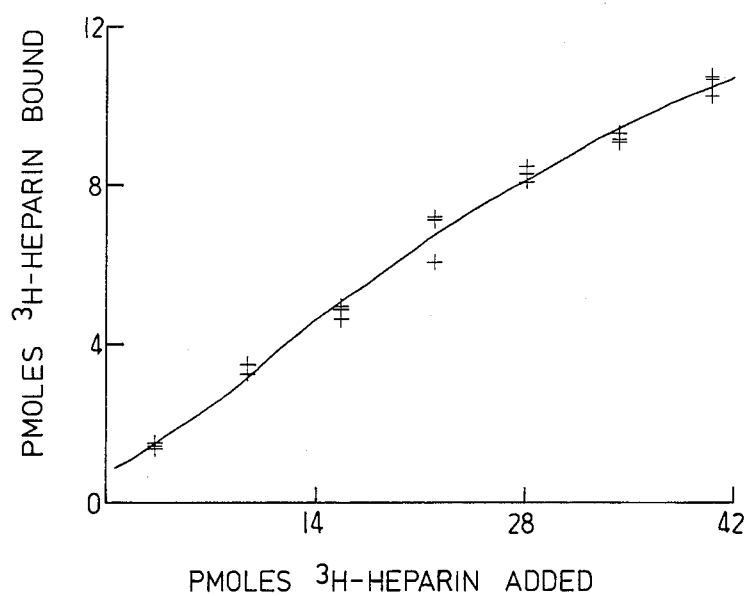

It ha been discovered that the binding affinity of certain GAGs to binding sites on mammalian sperm and, in particular, the binding affinity and thus the dissociation constants for heparin with respect to certain heparin binding sites on such sperm are significantly correlated with the fertility of the male providing the sperm. For example, it has been found that bovine male fertility is significantly related to dissociation constants for the binding of heparin to sperm taken from the bulls being tested, the fertility of such bulls being indicated by the nonreturn rates calculated for each bull on at least 2000 first services in the previous calendar year. Such dissociation constants have been found to be inversely related to fertility, so that a relatively high binding affinity (corresponding to a low dissociation constant) is associated with high fertility and a relatively low binding affinity (corresponding to a high dissociation constant) is associated with low fertility.

Once it has been established that a given male is fertile at least to some degree, descriptions of fertility of necessity must be in relative terms. Consequently, the fertility of a bull to be tested must be compared to that of either another individual or a selected group of individuals. Alternatively, the fertility of the male to be tested may be compared to a standard established by the testing of a large number of males of like species.

The method of the invention for evaluating the fertility of a male mammal includes collecting a semen sample, herein denoted the "test semen," containing sperm from the mammal whose fertility is to be evaluated. The binding affinity of a selected GAG to the sperm of the test semen then is measured by use of a suitable means for measuring binding affinity. The binding affinity of the GAG to the sperm of the test semen is compared to the binding affinity determined by like means, of the GAG to the sperm of control semen collected from control males. The fertility of the male to be evaluated may be judged to be high or low relative to the fertility of the control males by the degree to which the binding affinity of the GAG to the sperm of the test semen is higher or lower than the binding affinity of the GAG to the sperm of the control semen.

Preferably, the GAG referred to above is heparin, and its affinity for sperm binding sites is perceived by measuring the dissociation constant of heparin with respect to selected binding sites on the sperm. The data reported in Handrow, et al., referred to above, suggested that multiple classes of binding sites and affinities for heparin exist on bovine sperm. Furthermore, preparations of heparin are extremely heterogeneous and can easily possess molecular weights ranging from 5,000 to 50,000, as is reported in G. H. Barlow (1983), "Molecular Weight Distribution Determination on Heparin Samples." *Thromb. Res*, 31, 513. It is advantageous that heparin being used in a saturation assay or equivalent method of determining binding affinity or a dissociation constant have a molecular weight within a limited range, preferably not varying by substantially more than 3,000. For example, heparin within the molecular weight of 13,000–15,000 was used in example 1, set forth below, for saturation assays and was found to be satisfactory. It is also convenient to so adjust concentrations and method that binding affinity is measured with respect to a known number of classes of binding sites and preferably only to the primary class.

Those skilled in the art are aware of a variety of means for measuring binding affinities or determining dissociation constants, including affinity chromatography and the use of saturation binding assays utilizing radioactively, fluorescently, or otherwise labeled materials. Yet another method is the use of fluorescent materials and digital imaging. All such alternative methods of evaluating binding affinities or determining dissocation constants are within the scope and spirit of the invention. One preferred method, as described in example 1, below, is the performance of a saturation binding assay using tritium labeled heparin, referred to herein as "$^3$H-heparin." In the discussions of saturation binding assays set forth below, the use of $^3$H-heparin shall be described as typical of labeled heparin techniques.

The use of saturation binding assays as a means for measuring the binding affinity of a test material to a binding site is familiar to those skilled in the art. A saturation binding assay is an assay in which first the binding site to be examined is flooded with an original quantity of the test material the binding characteristics of which are to be evaluated. Then the binding site is exposed to additional test material that is distinguishable from the original test material. Then the amount of the additional test material that substitutes for that original test material that had been bound to the binding sites is measured. Generally this is done in a series of replications in which increasing amounts of the additional test material is added and any corresponding increase in the additional test material substituted is noted. A higher affinity of the test material to the binding site corresponds to a lesser amount of substitution.

Substitution may be measured by using a radioactively, fluorescently, or otherwise labeled test material. The labeled test material is most commonly that which is utilized as the additional test material after the binding sites have already been flooded with the original quantity of unlabeled test material. However, procedures are possible in which the labeled test material is used as the original quantity first bound to the binding sites. In either event, substituted amounts can be discerned by measuring directly or indirectly the label retained on the binding sites. Conventional means of measuring radioactivity, change in intensity of color or opacity, and the sort may be used. If fluorescent labeling is used, retained test material can be measured and binding sites can be directly evaulated by means of fluorescence microscopy and computerized digital image analysis. All of these methods and the nature and techniques involved in conducting saturation binding assays and in determining dissociation constants are well known to those skilled in the art.

The work of Handrow, et al. referred to above included characterization of the binding of $^3$H-heparin to bull sperm. In that study, data was collected and treated after the method of G. Scatchard (1949), "The Attractions of Proteins for Small Molecules and Ions." *Ann. NY Acad. Sci.*, 51, 660. In the Handrow, et al. study, the Scatchard plots were curvilinear, suggesting that multiple classes of binding sites exist having differing affinities. In the Handrow, et al. study, unlabeled heparin was used to displaced $^3$H-heparin to obtain the Scatchard data, and the assumption was made that the labeled and unlabeled heparin competed equally for the binding sites.

For the reasons set forth above, preferably the method of the invention utilizes for performing saturation binding assays only $^3$H-heparin having a narrow range of molecular weight, and particularly a molecular weight of 13,000 to 15,000. Furthermore, the assays preferably are performed using doses of $^3$H-heparin that are in a range that can be anticipated to yield a substantially linear plot of data calculated after the method of Scatchard. In the assays reported as example 1, below, logistic equations also were used to compute the dose of $^3$H-heparin that was required to obtain 50% saturation. Those calculations and the calculations in accord with Scatchard yielded similar estimates of the dissociation constants for the sperm subjected to the method of the invention, and the Scatchard data in fact proved to be substantially linear.

These findings suggest that, under the conditions of example 1, only a primary binding site for heparin on sperm was being compared among the bulls tested. Heparin and heparan sulfate are knwon to compete for the same binding sites on the cell surface. See L. Kjellen, et al., (1977), "Binding of Heparin and Heparan Sulfate to Rat Liver Cells." *Biochem. Biophys. Res. Comm.*, 74, 126. Consequently, heparan sulfate may be substituted for heparin in carrying out the method of the invention. Similarly, other GAGs besides heparin have proved to be effective in promoting acrosome reactios in bull sperm, their potencies being related to the degree to which they are sulfated, as was shown in the Handrow, et al. study referred to above. Chondroitin sulfate isomers have been shown to be less effective, or even ineffective at displaying $^3$H-heparin from bull sperm. See R. R. Handrow, et al., (1984), "Specific Binding of the Glycosaminoglycan $^3$H-heparin to Bull, Monkey, and Rabbit Spermatozoa In Vitro." *J. Androl.*, 5, 51.

It may be anticipated that separate binding sites exist for the other various GAGs known to interact with mammal sperm to promote acrosome reactions. For example, chondroitin sulfate B is known to promote acrosome reactions in some mammal sperm. By use of assay techniques comparable to those used in the Handrow, et al. study of tritium heparin referred to above, it has now been discovered that a primary binding site exits on mammalian sperm for chrondroitin sulfate B. From the examples of heparin, heparin sulfate, and chondroitin sulfate B, it can be predicted that comparable binding sites exist for the other various GAGS known to interact with mammal sperm, allowing the affinity of those GAGS for mammal sperm to likewise be used to predict the fertility of males.

The examples below provide specific examples of the invention disclosed herein, although the invention is not to be understood as limited in any way to the terms and scope of the examples.

EXAMPLE 1

Demonstration of the Efficacy of the Method, Utilizing Saturation Binding Assays Semen samples were collected by artificial vagina from ten mature Holstein bulls. 59–90 day nonreturn rates had been computed for each of these bulls on at least two thousand first services in the previous calendar year. Thus, a specific service of a cow was deemed a "nonreturn" if, the cow being bred on a given day, the cow was not bred again between the 59th and 90th day thereafter. Such calculations of nonreturn rates are conventional in the bovine artificial insemination industry. All the bulls sampled were active in commercial artificial insemination at the time of semen collection and all produced semen commanding a comparable price.

Semen samples were obtained weekly, always being collected on the same day of the week, for up to five consecutive weeks. First and second ejaculates were obtained, when possible. One bull was collected only once. His sperm were used in every $^3$H-heparin binding assay described to compute intra- and inter-assay coefficients of variance. The sperm were pelleted from seminal plasma by centrifugation at 800 xg for ten minutes. The pelleted sperm were then resuspended in 40 mM Tris buffer containing 10% sucrose. The resuspended sperm were stored in liquid nitrogen at $-196°$ C.

Binding assays were conducted in the following manner. Sperm cells suspensions to be tested were removed from the liquid nitrogen and thawed in a 37° C. waterbath. Samples were transferred to 12×75 mm test tubes and centrifuged at 800 xg for ten minutes to pellet the sperm again. The pellets of sperm were then resuspended in 40 mM Tris buffer. Portions of the suspension of sperm sufficient to contain 2×10$^7$ sperm were pipetted into 12×75 mm test tubes.

Saturation binding assays were performed under equilibrium conditions in accord with the method of R. R. Handrow, et al., (1984), "Specific Binding of the Glycosaminoglycan ³H-heparin to Bull, Monkey, and Rabbit Spermatozoa In Vitro." *J. Androl.,* 5, 51. Seven concentrations of ³H-heparin ranging from $2.2 \times 10^4$ to $2.8 \times 10^5$ dpm were assayed in triplicate at each dose. The ³H-heparin (0.206 mCi/mg, m.w. 13,000–15,000) was obtained from New England Nuclear. Non-specific binding was determined in duplicate for each concentration of ³H-heparin by adding 1 mg of unlabeled heparin (obtained from Calbiochem) to incubation test tubes containing ³H-heparin and sperm suspensions. All of the assays were performed in a final volume of 1 ml using 40 mM Tris buffer with 2 mM $Ca^{2+}$ and 0.1% sodium azide, pH 7.35. Equilibrium conditions were obtained by incubating the incubation test tubes in a shaking waterbath for two hours at 37° C.

Assay incubations were terminated by filtering the suspensions onto glass membrane filters (Whatman 934-AH) placed on a Millipore sampling manifold. Incubation test tubes and glass membrane filters were washed with 1 ml of ice cold Tris buffer three times. The wet filters were then placed into polyethelene scintillation minivials and 4 ml scintillation fluid (3a70B, Research Products International) were pipetted into each scintillation minivial. The radioactivity in each minivial was monitored with a Packard Tri-Carb liquid scintillation spectrophotometer having a machine efficiency of 24%.

To normalize binding data among the various bulls, DNA was assayed in each original semem sample in accord with the method of C. Labarca and K. Paigen, (1980), "A Simple, Rapid, and Sensitive DNA Assay Procedure." *Anal. Biochem.,* 102, 344. Binding data for ³H-heparin were then computed according to the method Scatchard referred to above. Estimates of the binding affinities and numbers of binding sites were obtained by using a direct fit line in accord with the method of N. A. C. Cressie and D. D. Keightley, (1979), "The Underlying Structure of the Direct Linear Plot With Application to the Analysis of Hormone-Receptor Interactions," *J. Steroid Biochem.,* 11, 1173. All calculations and the direct fit program were performed on a Hewlett-Packard 9835A computer. Separate calculations were peformed to compute the dose of ³H-heparin needed to obtain 50% saturation. These calculations were performed using logistic equations in accord with the method of D. Rodbard, (1976), "Estimation of Molecular Weight by Gel Filtration and Gel Electrophoresis, II. Statistical and Computational Considerations." *Methods of Protein Separation,* Vol. 2, N. Catsimpoolas, ed. (Plenum Press, NY), Ch. 4. Analysis of variance was used to test for differences in affinities and numbers of binding sites among bulls, between first and second ejaculates, and across successive weeks of collection.

Figure 2:
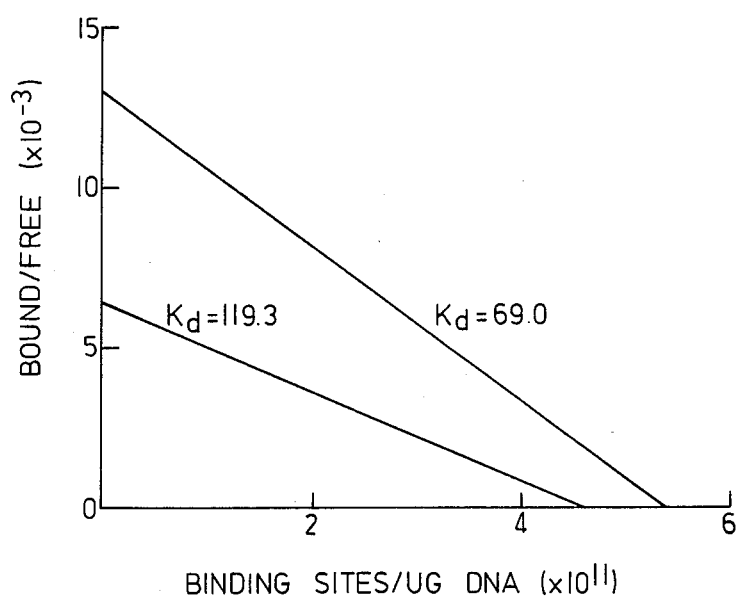

The results are presented in the figures. FIG. 1 is a representative saturation plot for binding of ³H-heparin to bull sperm. The results correspond generally to the results shown in R. R. Handrow, et al., (1984), "Specific Binding of the Glycosaminoglycan ³H-heparin to Bull, Monkey, and Rabbit Spermatozoa In Vitro." *J. Androl.,* 5, 51, referred to above. FIG. 2 shows two Scatchard plots with direct fit lines. The bulls were divided into two groups, those with 59–90 day nonreturn rates above or below the average nonreturn rate of 71%. The two groups were designated as having high and low fertility, respectively. Data from each of the groups were combined for computation of the Scatchard plots presented. The average nonreturn rate was $74.8 \pm 1.6$(SD) for the high fertility group and $66.9 \pm 2.6$(SD) for the low fertility group. The $K_d$ calculated for the high fertility group was 69.0 and the low fertility group was 119.3.

Table 1, below, contains the dissociation constants, numbers of binding sites, and laboratory evaluations of sperm characteristics observed in the original ejaculates for each bull, the bulls being listed in descending order of nonreturn rate. No significant differences were found in binding characteristics between first and second ejaculates or among successive weeks of collection. Consequently, average values are reported. The incidences of primary and secondary abnormal sperm did not vary significantly among the bulls.

When binding data for the high and low fertility groups as presented in Table 1 were averaged, a significant difference existed in dissociation constants (p less than 0.01), but no statistical difference existed in the number of binding sites. See Table 2. The dissociation constants were computed to be $69 \pm 21$(SD) and $119 \pm 27$(SD) picomoles for the high and low fertility groups, respectively. Table 2 also contains the dose of ³H-heparin that was required to obtain 50% saturation ($ED_{50}$) based on logistic equations. The ($ED_{50}$) was computed to be $69.4 \pm 15.7$(SD) and $139.7 \pm 16.3$(SD) picomoles for the high and low fertility groups, respectively. These figures agreed with the dissociation constants calculated from the Scatchard data.

TABLE 1

Dissociation constants ($K_d$) and numbers of binding sites for ³H—heparin for bull sperm. Also shown are the percentages of primary and secondary abnormal sperm[a].

| Bull code[b] | n[c] | $K_d$ (pmoles) | Binding Sites/ ug DNA[d] | Abnormal Sperm (%) Primary | Secondary |
|---|---|---|---|---|---|
| A | 7 | 45.5 (7.6) | 3.3 (.4) | 2.0 (1.4) | 7.6 (8.4) |
| B | 10 | 70.4 (14.2) | 4.0 (.1) | 3.4 (.7) | 3.3 (.9) |
| C | 10 | 89.0 (26.1) | 4.7 (.9) | 3.0 (1.5) | 2.4 (1.3) |
| D[e] | 21 | 44.9 (4.8) | 10.3 (9.0) | 2.7 (.3) | 3.8 (1.3) |
| E | 2 | 95.4 (14.6) | 4.8 (.1) | 2.5 (.1) | 2.9 (.3) |
| F | 10 | 99.8 (14.1) | 4.0 (.6) | 3.7 (1.7) | 2.5 (1.2) |
| G | 8 | 100.3 (17.4) | 3.9 (.4) | 7.2 (1.8) | 3.1 (1.8) |
| H | 9 | 168.8 (20.3) | 4.2 (.3) | 2.8 (1.0) | 4.6 (1.4) |
| I | 10 | 100.0 (15.4) | 4.7 (.7) | 6.8 (.9) | 4.4 (2.8) |
| J | 10 | 127.6 (37.5) | 6.1 (1.9) | 3.1 (1.6) | 11.3 (2.9) |

[a]Expressed as mean (SD).
[b]Bulls are listed in descending order of 59–60 day nonreturn rates. The average nonreturn rates for bulls A through E and bulls F through J were $74.8 \pm 1.6$ (SD) and $66.9 \pm 2.6$ (SD), respectively.
[c]n = # of ejaculates except bull D as stated in Methods.
[d]($\times 10^{11}$).
[e]Internal standard.

TABLE 2

Dissociation constants, $ED_{50}$[a], and numbers of binding sites for ³H—heparin to sperm from bulls of high and low fertility.

| | Mean (SD) | | |
|---|---|---|---|
| Relative Fertility | $K_d$ (pmoles) | $ED_{50}$ (pmoles) | binding sites/ ug DNA[b] |
| High | 69.0 (21.1) | 69.4 (15.7) | 5.4 (2.5) |
| Low | 119.0 (27.0)[c] | 139.7 (16.3)[c] | 4.6 (.8) |

[a]The dose of ³H—heparin required for 50% saturation.
[b]($\times 10^{11}$).
[c]p less than .01 compared to high fertility bulls.

From the work and results reported as this example, it can be seen that dissociation constants associated with the binding of heparin to bull sperm, measured and calculated by conventional means, are significantly related to nonreturn rates of dairy bulls and thus may be used to predict relative fertility of bulls.

EXAMPLE 2

Hypothetical Example of the Use of Affinity Chromatography to Measure the Binding Affinity of Heparin to Sperm Sperm from bulls to be tested may be collected, processed, and (if desired) stored in liquid nitrogen and rewarmed in accord with the procedures described in Example 1. Then the heparin binding sites may be solubilized by means of exposure to a detergent such as sodium dodecyl sulfate, benzethonium chloride, octyl glucoside, and comparable detergents such as those sold by Sigma Chemical Co. of St. Louis, Mo., as CHAPS, Triton X-100, or Hyamine or by Calbiochem of San Diego, Calif., as Zwittergent. Appropriate concentrations of detergent for such use will range from approximately 0.01% to 1.0% by weight, with concentration varying with the particular detergent in a manner well known to or readily determinable by those skilled in the art. Solubilization of the binding sites should be accomplished in a standard buffer such as TRIS, TALP, or a conventional acetate buffer. Preferably sperm is suspended in such a buffer for binding site solubilization in a concentration equivalent to approximately 20 to $50 \times 10^6$ sperm per ml. After solubilization, the solubilized material bearing the binding sites may be concentrated by lyophilization and prepared for conventional affinity chromatography.

Conventional affinity chromatography then may be used to comparatively evaluate the affinity of the solubilized binding sites for a selected glycosaminoglycan. An affinity column may be prepared utilizing an appropriate solid support bead such as Sepharose or agarose beads. Then an appropriate glycosaminoglycan, such as heparin, may be coupled to the beads to saturate the column therewith. A sample of the solubilized binding sites prepared as just disclosed than may be introduced onto the top of the column and allowed to reach equilibrium binding to the glycosaminoglycans on the beads. Unbound protein material may be washed free of the column with equilibrating buffer or other appropriate fluids. The bound material then may be subjected to aqueous solutions of an appropriate salt of increasing concentration. Sodium chloride is an appropriate salt, in which case either a linear or a stepwise gradiant of sodium chloride may be employed beginning at or about 0.2 M increasing to 2.0 M. The salt should be dissolved in a standard buffer. Alternatively, a solution of the glycosaminoglycan may be used to elute the bound material.

Fractions eluting from the column may then be collected in test tubes and the protein in each fraction estimated by measuring the absorbance of light at 280 nm in a conventional spectrophotometer. Bound material having a higher affinity for the glycosaminoglycan coupled to the affinity column will require a higher concentration of salt before it dissociates from the column. By this means, the relative affinity of the binding sites present on the sperm being evaluated for the selected glycosaminoglycan may be determined by a method that requires no use of radioactive materials or of a glycosaminoglycan marked in any way.

EXAMPLE 3

Alternative Example of the Use of Affinity Chromotography to Measure the Binding Affinity of Heparin to Sperm Sperm from bulls to be tested was collected, processed, stored in liquid nitrogen, and rewarmed in accord with the procedures described in Example 1. Then the entire plasma membrane and acrosomal membrane of the sperm were extracted by the following procedure. 10 ml of 50 mM $MgCl_2$ in 50 mM Tris, pH 6.1, was added to a pellet of washed sperm, and the sperm was suspended by gentle vortexing. The suspension was then cooled on ice for forty minutes. The suspension then was centrifuged at 2000 xg for ten minutes, and the supernatant containing the plasma and outer acrosomal membranes was recovered and dialyzed against water and then lyophilized. The inner acrosomal membranes then were extracted from the sperm by resuspending the pellet of sperm in 10 ml of 0.1% benzethonium chloride (obtained as "Hyamine 1622" from Sigma Chemical Co. of St. Louis, Mo., 0.1% Triton X-100 in 50 mM Tris, pH 6.1. The resuspended material was allowed to cool on ice for fifteen minutes and then was centrifuged at 12,100 xg for ten minutes. The supernatant was recovered and dialyzed against water. It was then lyophilized. The lyophilized membranes then were resuspended in 50 mM Tris, 2 mM $Ca^{2+}$, 0.01% sodium azide, pH 7.35. Approximately 4 O.D.$_{280}$ units were added to an affinity column prepared by saturating Sepharose beads with heparin. The column with the added sample was added to remain undisturbed for approximately forty-five minutes to allow binding to occur.

The protein sample placed on the column was then eluted by passing a solution of NaCl through the column. The eluting solution was a 100 ml linear gradient from 0 to 3M NaCl in 50 mM Tris, 2 mM $Ca^{2+}$, and 0.01% sodium azide, pH 7.35. The flow rate was set at 1 ml/min. 3 ml fractions were collected and examined for protein by absorbance at 280 nm.

A peak of protein was found to elute at 0.3M NaCl, presumably from the inner acrosomal membranes. Two additional protein peaks elute presumably from the outer acrosomal and plasma membrane material at 0.5M NaCl and after 3M NaCl. Thus, the method utilized in this example illustrates an alternative means for evaluating the relative affinity of the binding sites present on the sperm for heparin again utilizing a method that requires no use of radioactive materials or of a glycosaminoglycan marked in any way.

EXAMPLE 4

Figure 3:
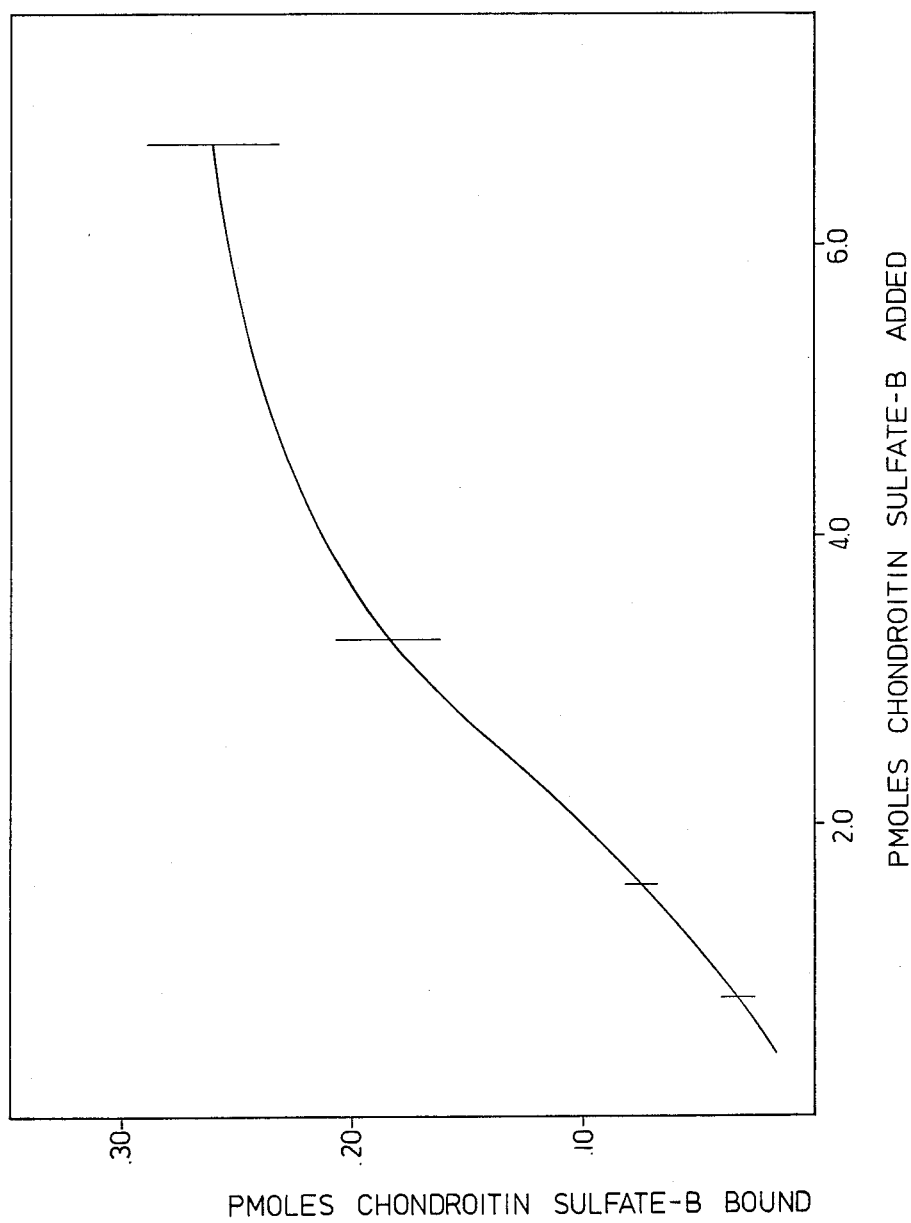

Demonstration of the Existence of a Primary Binding Site on Mammallian Sperm for Chondroitin Sulfate B Chondroitin sulfate B was isolated from follicular fluid by conventional techniques well known to those skilled in the art. Then the chondroitin sulfate B was labeled with tritium, also by conventional means. Saturation binding assays were then performed under equilibrium conditions in accord with the method of Example 1 and of R. Handrow, et al., (1984), "Specific Binding of the Glysoaminoglycan $^3$H-heparin to Bull, Monkey, and Rabbit Spermatozoa In Vitro." *J. Androl.*, 5, 51, substituting the tritium-labeled chondroitin sulfate B for the tritium-labeled heparin used by Handrow, et al. FIG. 3 corresponds to FIG. 1 and is a saturation plot for the binding of $^3$H-chondroitin sulfate B to bull sperm. The results suggest that a primary binding site exists for chondroitin sulfate B, as well as secondary or tertiary sites. These results correspond qualitatively to those obtained by the work reported as Example 1 and verify the existence of a primary binding site for chondroitin sulfate B suitable for employment in carrying out the method of the invention.

EXAMPLE 5

Hypothetical Example of the Use of Saturation Binding Assays for Chondroitin Sulfate B in Predicting the Fertility of Male Mammals Saturation binding assays for chondroitin sulfate B in all ways comparable to those described in Example 1, above, for heparin may be conducted utilizing $^3$H-chondroitin sulfate B. Chondroitin sulfate B can be isolated form folicular fluid or from female reproductive tract secretions and then may be labeled with tritium, all by conventional means familiar to those skilled in the art. It may be predicted that the relationship between dissociation constants, binding affinities, and male fertility reported with respect to heparin in Example 1 will be comparable to the corresponding relationships for chrondroitin sulfate B.

EXAMPLE 6

Hypothetical Example of the Use of Affinity Chromotography to Measure the Binding Affinity of Chondroitin Sulfate B to Sperm The procedures described in Example 2 with respect to heparin may be conducted in substantially the same way with chondroitin sulfate B substituted for heparin. Comparable results may be predicted.

EXAMPLE 7

Hypothetical Example of the Use of a Fluorescently Labeled GAG to Conduct Saturation Binding Assays with Sperm GAGS may be labeled with Conventional fluorescent materials, such as fluorescein, rhodamine, acridine orange, or Texas red, all by conventional means for so fluorescenating such materials. The method of Example 1 may then be employed, substituting the fluorescenated GAG for the radioactively labeled GAG described in Example 1. Any necessary minor adjustments to the method that might be necessary would be well within the scope of the skill and knowledge of one skilled in the art. The fluorescence of samples would be measured instead of the radioactivity, a step that could be conducted by such conventional means as computer enhanced digital imaging or a spectrophotometer.

It will be readily apparent to those skilled in the art that a number of modifications and changes can be made in the invention as disclosed without departing from the spirit and scope of the present invention. Therefore, it is not intended that the invention be limited by the terms of the examples and disclosure above but only by the claims set forth below.

What is claimed is:

1. A method for evaluating the fertility of a test male mammal relative to the fertility of a control male mammal comprising the steps of:
   (a) collecting samples of semen from the test male and the control male; and
   (b) measuring the binding affinity of a selected glycosaminoglycan to the sperm of the semen samples by a selected means for measuring binding affinities, whereupon the fertility of the test male may be evaluated, as higher or lower than that of the control male by the degree to which the binding affinity of the glycosaminoglycan to its sperm is higher or lower than the binding affinity of the glycosaminoglycan to the sperm of the control male.

2. The method of claim 1 wherein the glycosaminoglycan is selected from the group consisting of heparin, heparan sulfate, and chondroitin sulfate B.

3. The method of claim 1 wherein the means for measuring binding affinities includes means for measuring the dissociation constant of the glycosaminoglycan with respect to selected binding sites on the sperm, and fertility of the test male may be evaluated as higher or lower than that of the control male by the degree to which the dissociation constant associated with its sperm is lower or higher respectively than the dissociation constant associated with the sperm of the control male.

4. The method of claim 1 wherein the means for measuring the binding affinity is a saturation binding assay.

5. The method of claim 4 wherein the glycosaminoglycan is heparin and the molecular weight of the heparin used in the saturation binding assay is between thirteen thousand and fifteen thousand.

6. The method of claim 1 wherein the means for measuring binding affinities is a means for measuring binding affinity with respect to a known number of classes of binding sites.

7. The method of claim 6 wherein the means for measuring binding affinity measures binding affinity with respect only to a primary class of binding site.

8. The method of claim 1 wherein the means for measuring binding affinities is affinity chromatography.

9. The method of claim 8 including the step of solubilizing the sites of the sperm capable of binding the glycosaminoglycan and the means for measuring binding affinities includes subjecting the solubilized binding sites to affinity chromatography.

10. The method of claim 8 including the steps of extracting the plasma and acrosomal membranes of the sperm and the means for measuring binding affinities includes subjecting the extracted membranes to affinity chromatography.

11. The method of claim 1 wherein the control male is represented by males previously evaluated for fertility to establish binding affinities characteristic of males exhibiting high and low fertility.

12. The method of claim 1 wherein the means for measuring binding affinities includes exposing sperm to a fluorescent-labeled glycosaminoglycan and detecting bound, labeled glycosaminoglycan by use of means to detect and analyze fluroescence.

13. The method of claim 12 wherein the means to detect and analyze fluorescence includes fluorescence microscopy.

14. The method of claim 12 wherein the means to detect and analyze fluorescence includes digital image analysis.

* * * * *